US00PP09921P

United States Patent [19]

Dümmen

[11] Patent Number: Plant 9,921

[45] Date of Patent: Jun. 10, 1997

[54] GERANIUM PLANT NAMED HWD MARAVILLIA

[75] Inventor: Günter Dümmen, Rheinberg-Eversael, Germany

[73] Assignee: Dümmen Jungpflanzenkulturen, Rheinberg-Eversael

[21] Appl. No.: 614,438

[22] Filed: Mar. 13, 1996

[51] Int. Cl.[6] ..... A01H 5/00

[52] U.S. Cl. ..... Plt./87.12

[58] Field of Search ..... Plt./87.12

*Primary Examiner*—James R. Feyrer
*Attorney, Agent, or Firm*—C. A. Whealy

[57] ABSTRACT

A new and distinct cultivar of Geranium plant named HWD Maravillia, characterized by its semi-double bright red purple flowers with purple spots at the base of the petals; compact to medium plant size; medium to large umbels; large flower size; and freely branching plant habit.

1 Drawing Sheet

The present invention relates to a new and distinct cultivar of Geranium plant, botanically known as *Pelargonium ×hortorum*, known as the variety Duemar, and hereinafter referred to by the cultivar name HWD Maravillia.

The new cultivar is a product of a planned breeding program conducted by the inventor in Rheinberg, Germany. The objective of the breeding program was to develop a new freely branching, semi-double geranium with bright red purple-colored flowers.

The new cultivar originated from a cross made by the inventor of the nonpatented cultivar Contesta as the male or pollen parent with the proprietary selection 86-5-5 as the female or seed parent.

The cultivar HWD Maravillia was discovered and selected by the inventor as a flowering plant within the progeny of the stated cross in a controlled environment in Rheinberg, Germany. Asexual reproduction of the new cultivar by terminal cuttings taken at Rheinberg, Germany, has shown that the unique features of this new Geranium are stabilized and reproduced true to type in successive generations of asexual reproduction.

The following traits have been repeatedly observed and are determined. to be the unique characteristics of HWD Maravillia. These characteristics in combination distinguish HWD Maravillia as a new and distinct cultivar:

1. Semi-double bright red purple flowers with purple spots at the base of the petals.
2. Compact to medium plant size.
3. Medium to large umbels.
4. Large flower size.
5. Freely branching.

In comparision to the parent cultivar Contesta, plants of the new Geranium are larger, more freely branching, and have darker green leaves and larger flowers. In comparison to the parent selection 86-5-5, plants of the new Geranium are shorter, more freely branching and have larger flowers.

The new Geranium is similar in petal color to the cultivars Fox (disclosed in U.S. Plant Pat. No. 7,083), Americana Violet (disclosed in U.S. Plant Pat. No. 8, 750), Fisdino (disclosed in U.S. Plant Pat. No. 8,761), and HWD Campana (U.S. Plant Patent Applied For). Compared to plants of the cultivar Fox, plants of the new Geranium have lighter green foliage and petals do not have orange highlights. Compared to plants of the cultivar Americana Violet, plants of the new Geranium do not have zoned foliage and petals do not have orange spots. Compared to plants of the cultivar Fisdino, plants of the new Geranium do not have zoned foliage and petal spots are darker purple in color. Compared to plants of the cultivar HWD Campana, plants of the new Geranium do not have zoned foliage and petals have purple spots towards the petal base.

The accompanying colored photograph illustrates the overall appearance of the new cultivar, showing the colors as true as it is reasonably possible to obtain in colored reproductions of this type. Flower color appears lighter than the actual flower color due to light reflectance. The photograph comprises a top perspective view of a typical potted plant of HWD Maravillia with one plant in a 10-cm container.

The cultivar HWD Maravillia has not been observed under all possible environmental conditions. The phenotype may vary somewhat with variations in environment such as temperature and light intensity, without, however, any variance in genotype. The following observations, measurments and comparisons described plants grown in Rheinberg, Germany, under commercial practice in a glass-covered greenhouse with day temperatures of 24C and night temperatures of 18 to 20C and light levels of 45,000 to 60,000 lux. Plants were grown in 10-cm pots with one plant per pot.

In the following description, color references are made to The Royal Horticultural Society Colour Chart except where general terms of ordinary dictionary significance are used.

Classification:

*Botanical.*—*Pelargonium×hortorum.*

*Commercial.*—Zonal Geranium.

*Cultivar.*—HWD Maravillia.

Parentage:

*Male parent.*—Cultivar Contesta (not patented).

*Female parent.*—Proprietary selection 86-5-5.

Propagation:

*Type cutting.*—Terminal cuttings.

*Time to initiate roots.*—Summer: 27C, 21 days; winter: 20C, 28 days.

Plant description:

*General appearance.*—Rounded; compact to medium plant size; upright to somewhat spreading; freely branching.

*Foliage description.*—Arrangement: Mostly opposite, some alternate. Shape: Orbicular with rounded tip and cordate base. Size: Length: 8.5 to 9 cm. Width: 6 to 6.8 cm. Texture: Velvety, pubescent on upper and under surfaces. Margin: Crenate. Color: Young foliage, upper suface: 146A. Young foliage, under surface: 147B. Mature foliage, upper surface: 146A. Mature foliage, under surface: 147B. Veins, upper surface: 146D. Veins, under surface: 146D. Petiole:

146C. Venation pattern: Palmate. Petiole: Length: 4 to 6 cm. Diameter: 2 mm.

*Stem description.*—Internode length: 0.7 to 1.1 cm. Stem color: 146C. Lateral branch number: 8. Lateral branch length: 6 to 8 cm.

Flowering description:

*Flowering habit.*—Freely flowering. Flowers arranged in umbels.

*Natural flowering season.*—Year-round.

*Flowers borne.*—Flower buds develop in apical leaf axils. Umbels are displayed above the foliage.

*Quantity of inflorescences.*—Very floriferous; usually 7 to 8 open umbels and at least 7 developing umbels per plant at one time.

*Umbels.*—Form: Rounded. Diameter: 11 to 12 cm. Depth (height): 5 to 6 cm.

*Flowers.*—Form: Semi-double. Shape: Rounded. Quantity of flowers per umbel: 14. Diameter: 5.5 cm. Depth (height): 1.5 to 2 cm.

*Petals.*—Shape: Obovate with rounded tip. Arrangement: Rosette, overlapping. Quantity: 6 to 7. Aspect: Flat. Size: Length: 2.8 to 3 cm. Width: 2.2 to 2.4 cm. Texture: Satiny, smooth. Margin: Entire. Color: When opening, upper surface: 66B. When opening, under surface: 73B with margin of 66A, parallel veins of 66A, and white spot 5 mm in diameter on upper three petals towards petal base. Upper surface: 66B with dominate purple spot, 67A, 4 to 5 mm in diameter, and 5 to 6 mm from petal base. White spot 5 mm in diameter on upper three petals towards petal base. Petal color fades to 66D and eventually to white at base. Under surface: 66C becoming darker towards margin, 66A, parallel veins of 66A, and white spot 5 mm in diameter on upper three petals towards petal base. Petal color fades to white at base. Fading: No fading observed.

*Petaloids.*—Shape: Regular, generally obovate with rounded tip. Arrangement: Rosette, overlapping. Quantity: 3 to 4. Size: Length: 2.4 to 2.6 cm. Width: 1.8 to 2.1 cm. Texture: Satiny, smooth. Margin: Entire. Color: When opening, upper surface: 66B. When opening, under surface: 73B with margin of 66A, parallel veins of 66A, and white spot 5 mm in diameter on upper three petals towards petal base. Upper surface: 66B with dominate purple spot, 67A, 4 to 5 mm in diameter, and 5 to 6 mm from petal base. White spot 5 mm in diameter on upper three petals towards petal base. Petal color fades to 66D and eventually to white at base. Under surface: 66C becoming darker towards margin, 66A, parallel veins of 66A and white spot 5 mm in diameter on upper three petals towards petal base. Petal color fades to white at base. Fading: No fading observed.

*Peduncle (umbel stem).*—Angle: Erect to slightly bent near apex. Length: 12 to 15 cm. Pubescence: Fine. Color: 144A.

*Pedicel (individual flower stem).*—Angle: Erect, rigid. Length: 3 cm. Pubescence: Fine. Color: 59A with 144B at peduncle.

*Flower bud.*—Shape: Ovoid. Length: 1.5 cm. Diameter: 1 cm. Color: 62A.

*Sepals.*—Arrangement: Rosette. Quantity: 5. Size: Length: 1.1 cm. Width: 3 to 4 mm. Shape: Acuminate with apiculate tip. Texture: Velvety. Margin: Entire. Color: Upper surface: 144A with 60A near attachment to pedicel. Under surface: 144A with 60A near attachment to pedicel.

*Reproduction organs.*—Androecium: Stamen number: 12. Anther size: 2 mm. Anther color: 60A. Pollen color: 34B. Gynoecium: Pistil number: 1. Pistil length: 1 cm. Stigma shape: Decurrent. Stigma color: 57A. Style length: 4 mm. Style color: 57A. Ploidy level: Tetraploid.

Disease resistance: No fungal, bacterial nor viral problems observed.

Seed development: Seed production is very rarely observed.

It is claimed:

1. A new and distinct cultivar of Geranium plant named HWD Maravillia, as illustrated and described.

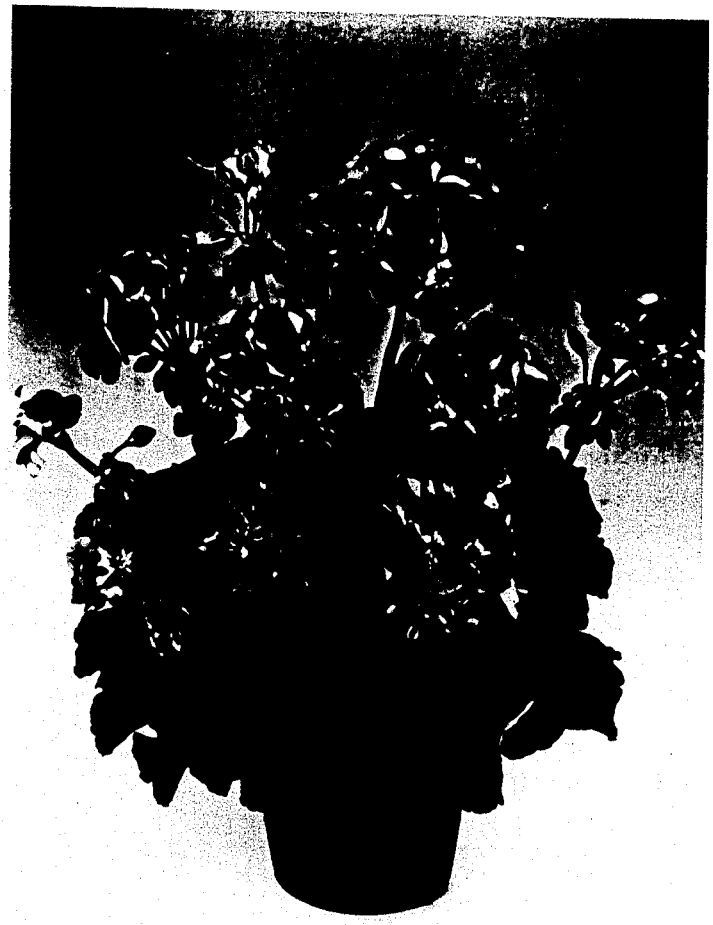

* * * * *